US010260868B2

(12) United States Patent
Durand De Gevigney et al.

(10) Patent No.: US 10,260,868 B2
(45) Date of Patent: Apr. 16, 2019

(54) INTERFEROMETRIC METHOD AND SYSTEM USING VARIABLE FRINGE SPACING FOR INSPECTING TRANSPARENT WAFERS FOR ELECTRONICS, OPTICS OR OPTOELECTRONICS

(71) Applicant: UNITY SEMICONDUCTOR, Monbonnot-Saint-Martin (FR)

(72) Inventors: Mayeul Durand De Gevigney, Chambery (FR); Philippe Gastaldo, Pontcharra (FR)

(73) Assignee: UNITY SEMICONDUCTOR, Montbonnot-Saint-Martin (FR)

( * ) Notice: Subject to any disclaimer, the term of this patent is extended or adjusted under 35 U.S.C. 154(b) by 43 days.

(21) Appl. No.: 15/515,407

(22) PCT Filed: Sep. 29, 2015

(86) PCT No.: PCT/EP2015/072368
§ 371 (c)(1),
(2) Date: Mar. 29, 2017

(87) PCT Pub. No.: WO2016/050738
PCT Pub. Date: Apr. 7, 2016

(65) Prior Publication Data
US 2018/0231370 A1 Aug. 16, 2018

(30) Foreign Application Priority Data
Sep. 29, 2014 (FR) ...................................... 14 59170

(51) Int. Cl.
G01B 11/24 (2006.01)
G01N 21/95 (2006.01)
(Continued)

(52) U.S. Cl.
CPC ...... *G01B 11/2441* (2013.01); *G01B 9/02034* (2013.01); *G01M 11/331* (2013.01);
(Continued)

(58) Field of Classification Search
CPC ............ G01B 11/2441; G01B 9/02034; G01B 2210/56; H01L 22/12; G01M 11/331; G01N 21/8806; G01N 21/9503
See application file for complete search history.

(56) References Cited

U.S. PATENT DOCUMENTS 4,030,830 A 6/1977 Holly
2002/0191179 A1 12/2002 Tukker et al.
(Continued)

OTHER PUBLICATIONS

International Search Report from International Patent Application No. PCT/EP2015/072368, dated Dec. 16, 2015.
(Continued)

Primary Examiner — Hwa Andrew Lee
(74) Attorney, Agent, or Firm — Greer, Burns & Crain, Ltd.

(57) ABSTRACT

An electronic wafer inspecting method includes:
rotating the wavelength transparent wafer,
emitting, from a light source coupled with an interferometric device, two light beams, to form, a measurement volume and having a variable inter-fringe distance within the volume, a time signature of a defect intersecting the measurement volume depending on an inter-fringe distance where the defect intersects the volume,
the device and the wafer arranged so that the measurement volume extends into a wafer region,
collecting the light scattered by the wafer region,
emitting a signal representing the variation in the intensity of the collected light per time,
(Continued)

detecting in the signal, a frequency of the intensity, the frequency being the time of the passage of a defect through the measurement volume, determining, based on the value of the inter-fringe distance at the location where the defect passes, the position of the defect.

11 Claims, 9 Drawing Sheets

(51) Int. Cl.
G01N 21/88 (2006.01)
G01M 11/00 (2006.01)
G01B 9/02 (2006.01)
H01L 21/66 (2006.01)

(52) U.S. Cl.
CPC ..... *G01N 21/8806* (2013.01); *G01N 21/9501* (2013.01); *G01N 21/9503* (2013.01); *H01L 22/12* (2013.01); *G01B 2210/56* (2013.01)

(56) References Cited

U.S. PATENT DOCUMENTS

| | | | |
|---|---|---|---|
| 2003/0011786 A1* | 1/2003 | Levy | G01N 21/211 356/600 |
| 2007/0097380 A1* | 5/2007 | De Groot | G01B 11/0675 356/511 |
| 2009/0195786 A1 | 8/2009 | Gastaldo | |
| 2011/0222071 A1* | 9/2011 | Grotkopp | B24B 37/013 356/503 |

OTHER PUBLICATIONS

Written Opinion from International Patent Application No. PCT/EP2015/072368, dated Dec. 16, 2015.

Lemaitre-Auger et al., "Integrated Laser Doppler Velocimeter for Fluid Velocity and Wall Friction Measurements" Proceedings of IEEE Sensors (2002), vol. 1, p. 78-82. (Abstract only).

* cited by examiner

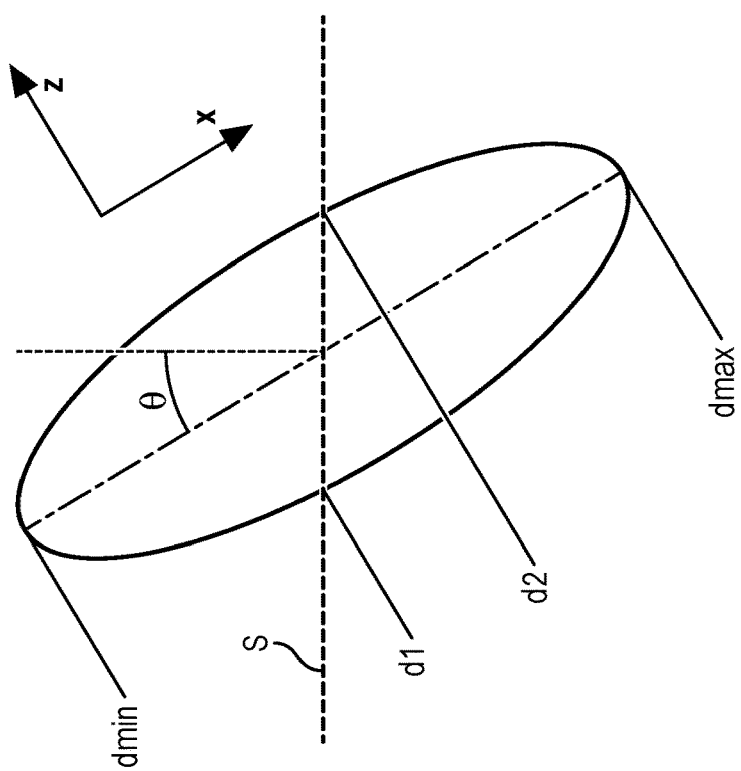
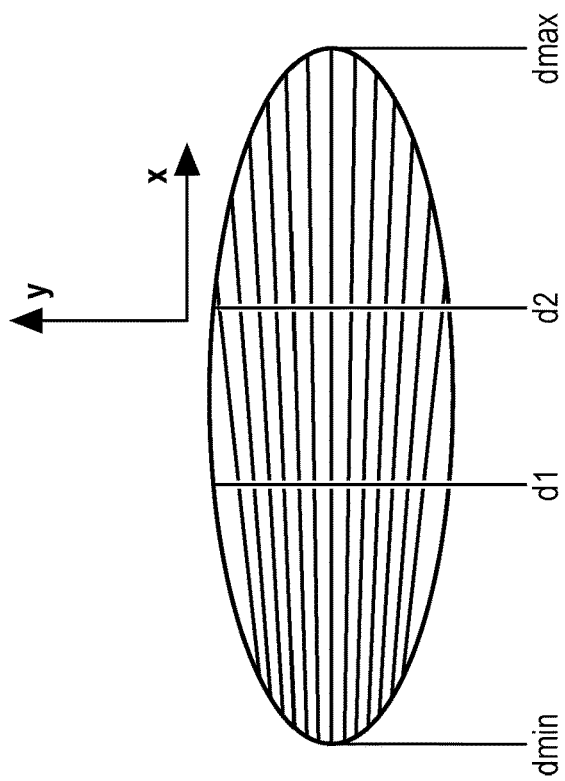
FIG. 3A
FIG. 3B

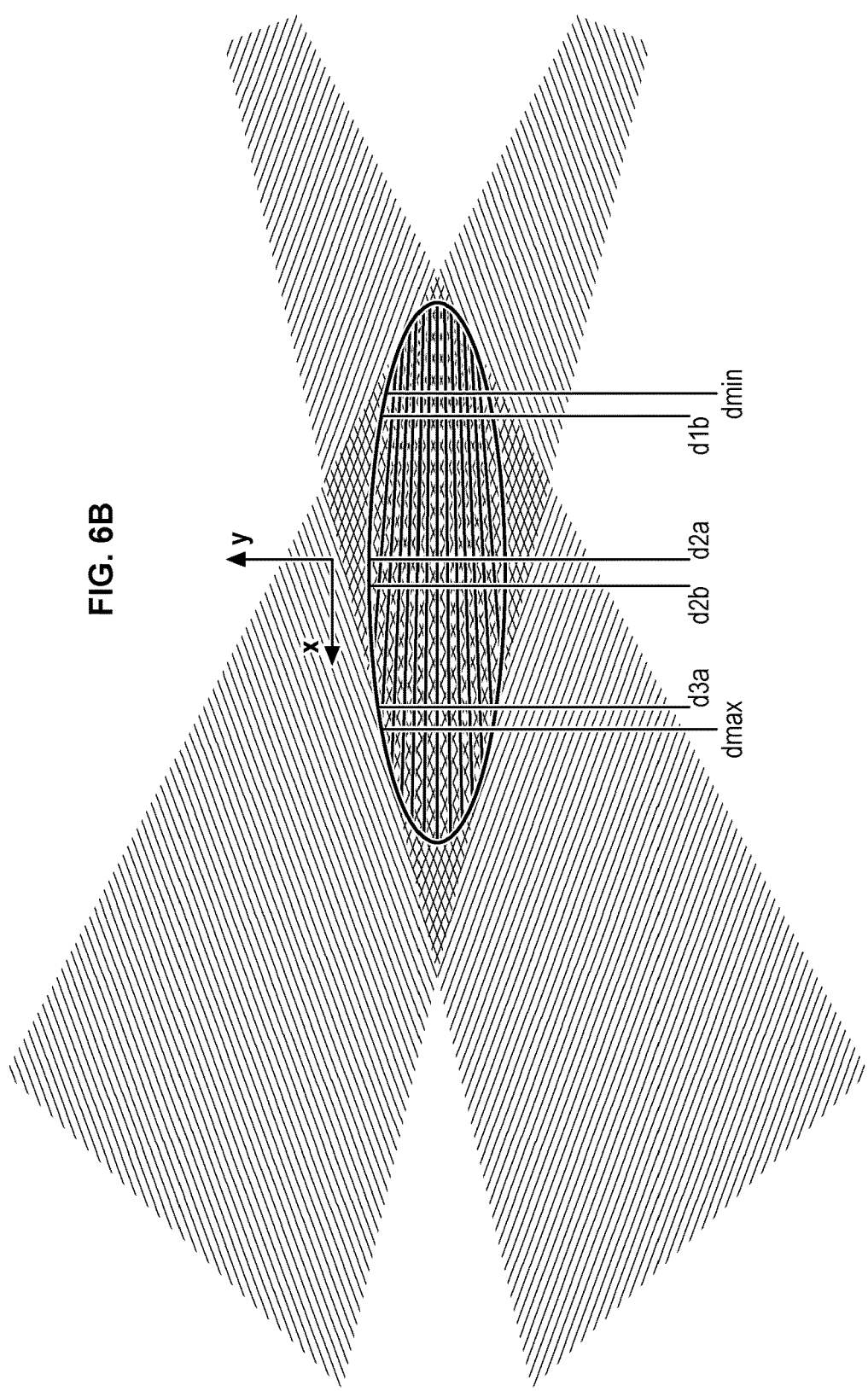

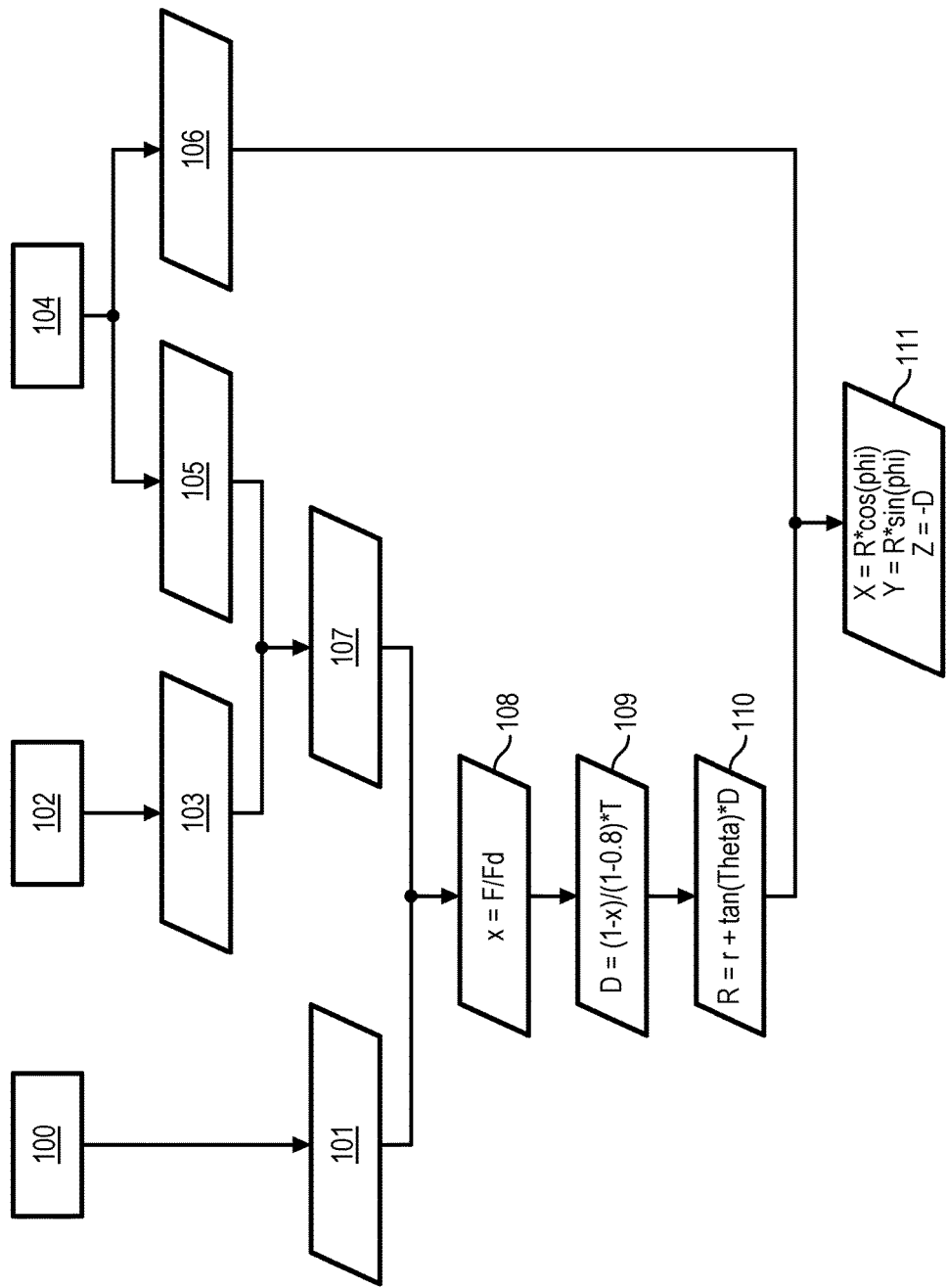

INTERFEROMETRIC METHOD AND SYSTEM USING VARIABLE FRINGE SPACING FOR INSPECTING TRANSPARENT WAFERS FOR ELECTRONICS, OPTICS OR OPTOELECTRONICS

BACKGROUND

The present invention relates to a method and a system for inspecting wafers for electronics, optics or optoelectronics, said wafers being partially or totally transparent at the wavelength of the light source used to carry out the inspection.

BACKGROUND OF THE INVENTION

During the manufacture and use of wafers for electronics, optics or optoelectronics, it is usual to carry out an inspection of the surface of each wafer so as to detect any defects.

On account of the very small size of the defects to be detected, a visual inspection by an operator is not sufficient.

Furthermore, the inspection is generally intended not only to discover the presence or absence of defects, but also to provide qualitative and/or quantitative information on said defects, such as their location, their size and/or their nature, for example.

Inspection systems have thus been developed with a view to detecting increasingly small defects and to provide all required information on the nature, the size, the location, etc. of said defects.

These systems must also allow a duration of inspection of each wafer that is sufficiently short so as not to adversely affect production speeds.

Various inspection techniques are known.

A first technique is Laser Doppler Velocimetry (LDV).

Document WO 2009/112704 describes a system for inspecting semi-conductor wafers implementing this technique. As shown in FIG. 1, this system comprises a light source 20 and an interferometric device 30 coupled with the light source arranged facing the surface S of the wafer 2 for inspection, which is actuated by a movement. Said interferometric device comprises a light guide the input of which is coupled with the light source and comprising two branches for dividing the beam originating from the light source into two incident beams. At the output of the optical waveguide, the two branches are oriented in relation to one another so as to form, at the intersection between the two beams, a measurement volume comprising a plurality of parallel fringes. The system also comprises an optical fibre 40 arranged between the surface of the wafer and a detection module 50, so as to guide the light backscattered by the surface of the wafer towards the detection module.

The presence of a defect on the surface of the wafer is indicated, when this defect crosses the interference fringes, by the scattering of a Doppler burst measured by the detection module. A Doppler burst is a signal that has a double frequency component: a low-frequency component, forming the envelope of the signal, corresponding to the mean light intensity scattered by the defect, and a high-frequency component, corresponding to the Doppler frequency containing the information on the velocity of the defect. The Doppler frequency fp is linked to the velocity v of movement of the defect in the direction perpendicular to the interference fringes and to the distance A between the interference fringes (or inter-fringe distances) by the relationship $v = f \ast \Delta$.

Document WO 02/39099 describes another system for inspecting semi-conductor wafers relying on laser Doppler velocimetry.

Another known technique for inspecting wafers is dark field microscopy, which consists of emitting a beam from a light source in the direction of the wafer and measuring the intensity of the light backscattered by the surface. A variation in the scattered intensity reveals the presence of a defect on the surface of the wafer.

These different techniques apply to wafers that are opaque at the wavelength of the beam.

On the other hand, no known technique allows satisfactory inspection of wafers that are at least partially transparent at the wavelength of the light source (said wafers being known as "transparent" hereinafter).

In fact, in this case, defects present on the surface of the wafer (on the face exposed to the light beam and/or on the opposite face) but also in the thickness of the wafer scatter the incident light and can therefore be detected. It is therefore impossible to know whether each detected defect is located on the surface for inspection or not.

The company KLA-Tencor proposes a system for inspecting transparent wafers called Candela™, of the laser scanning system and confocal detection type. However, this system is particularly difficult to focus due to the accuracy of positioning required for the confocal measurement, and therefore does not provide repeatable results.

SUMMARY

A purpose of the invention is to resolve the aforementioned problems and to design a system and method for inspecting transparent wafers that offers greater sensitivity and repeatability of the measurements than those of the known techniques.

According to the invention, a method is proposed for inspecting a wafer for electronics, optics or optoelectronics, comprising:
  rotating the wafer about an axis of symmetry perpendicular to a main surface of said wafer,
  emitting, from a light source coupled with an interferometric device, two quasi-collimated incident light beams, so as to form, at the intersection between the two beams, a measurement volume containing interference fringes extending transversally to the path of rotation of the wafer and having a variable inter-fringe distance within the measurement volume, the time signature of the passage of a defect through the measurement volume depending on the value of the inter-fringe distance at the location where the defect passes through the measurement volume, said wafer being at least partially transparent at the wavelength of the light source,
  the interferometric device and the wafer being arranged in relation to one another so that the measurement volume extends into a region of the wafer, the thickness of said region being less than the thickness of the wafer,
  collecting at least a portion of the light scattered by said region of the wafer,
  capturing the collected light and emitting an electrical signal representing the variation in the light intensity of the collected light as a function of time,
  detecting, in said signal, a frequency component in the variation of the intensity of said collected light, said frequency being the time signature of the passage of a defect through a measurement volume, determining, based on the value of the inter-fringe distance at the location where the defect passes, the position of said defect in the radial direction and/or in the thickness of the wafer.

According to a preferred embodiment, said interferometric device is an integrated optical device comprising an optical waveguide the input of which is coupled with the light source and which is divided into two branches, the output of which is oriented in order to form said measurement volume at the intersection of the two beams.

By "quasi-collimated beam" is meant a non-collimated bean having a small divergence, i.e. a non-zero divergence typically less than 20°.

Particularly advantageously, the inter-fringe distance varies in the radial direction of the wafer.

Preferably, the inter-fringe distance varies between a minimum distance at the end of the measurement volume the furthest from the axis of rotation of the wafer and a maximum distance at the end of the measurement volume that is the closest to the axis of rotation of the wafer.

According to an embodiment, in the measurement volume, the inter-fringe distance varies within an interval of ±50% around a nominal value.

According to an embodiment of the invention, mainly dedicated to determining the radial position of a defect, the measurement volume is inclined by an angle comprised between 10 and 80° with respect to the normal to the main surface of the wafer.

According to another embodiment of the invention, mainly dedicated to determining the position of a defect in the thickness of the wafer, the measurement volume is inclined by an angle comprised between 0 and 40° with respect to normal to the main surface of the wafer.

According to an embodiment, the method also comprises the implementation of a band-pass filtering of the signal, the pass-band of said filter being selected so as to transmit only the portion of the signal having the Doppler frequency associated with a determined position in the thickness of the wafer.

A further subject relates to a system for inspecting wafers for electronics, optics or optoelectronics, comprising:
- a device for driving a wafer in rotation about an axis of symmetry perpendicular to a main surface of said wafer,
- a light source suitable for emitting a quasi-collimated light beam the wavelength of which is chosen so that at least a portion of said beam is transmitted through the wafer,
- an interferometric device coupled with the light source in order to divide the beam emitted by said source into two beams and in order to form, at the intersection between the two beams, a respective measurement volume containing interference fringes, the inter-fringe distance being variable within said measurement volume,
- a device for collecting light scattered by the wafer,
- a device for capturing collected light configured in order to emit an electrical signal representing the variation in the light intensity of the collected light as a function of time,
- a processing device configured in order to detect, in said signal, a frequency component in the variation of the intensity of said collected light, said frequency being the time signature of the passage of a defect through a respective measurement volume and dependent on the value of the inter-fringe distance at the location where the defect passes through the measurement volume and in order to determine, based on said frequency, said value for the inter-fringe distance and the position of the defect in the radial direction and/or in the thickness of the wafer.

According to a preferred embodiment, the interferometric device is an integrated optical device.

Particularly advantageously, the system also comprises an arm for moving the interferometric device and the device for the collection of scattered light in translational motion in a radial direction.

BRIEF DESCRIPTION OF THE DRAWINGS

Other characteristics and advantages will become apparent from the detailed description that follows, with reference to the attached drawings in which:

FIGS. 3A and 3B show the measurement volume with respect to the surface of the wafer, respectively in a side view and in a top view, in a first embodiment of the invention, FIGS. 6A and 6B show the measurement volume with respect to the surface of the wafer, respectively in a side view and a top view, according to a second embodiment of the invention, FIG. 7 is a logic diagram showing the different steps for locating a defect in the volume of the wafer.

In the interests of clarity, the figures are not necessarily to scale.

DETAILED DESCRIPTION

The present invention relates to any wafer intended for use in the field of electronics, optics or optoelectronics, and being at least partially transparent at the wavelength of a beam emitted by a light source. In particular, the wafer can comprise at least one of the following materials: glass, sapphire, quartz, SiC, AsGa, GaN (non-limitative list).

Particularly advantageously, the invention avoids the constraints associated with the confocal technique by detecting defects by using a frequency signal, which can only be emitted by defects passing through a measurement volume created by a laser Doppler velocimeter.

In such a system, the positioning of the interferometric device must therefore be adjusted accurately with respect to the surface of the wafer for inspection, so that the wafer region for inspection passes through at least a portion of the measurement volume; on the other hand, the device for the collection of the backscattered light does not require an equally high positioning accuracy since the restriction of the measurement volume, and thus the detection, is carried out via the Doppler frequency.

Furthermore, as will be shown below in the description of particular embodiments, the invention makes it possible to detect defects with a higher resolution than the dimension of the measurement volume, in the radial direction and/or in the direction of the thickness of the wafer.

Figure 1:
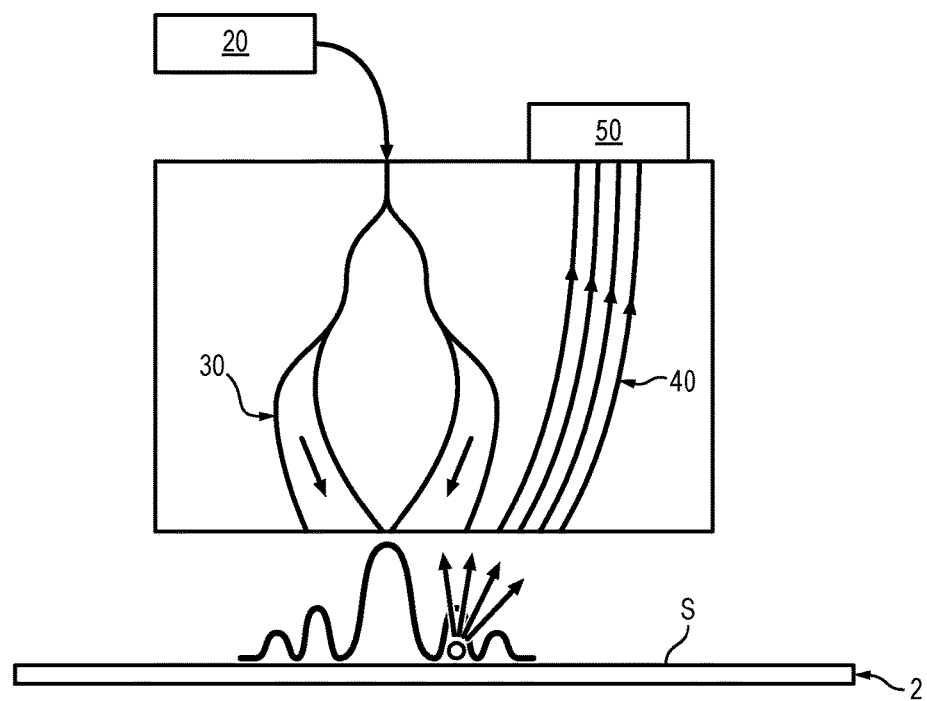
FIG. 1 is a schematic diagram of an inspection system based on laser Doppler velocimetry, described in the document WO 2009/112704.
Figure 2:
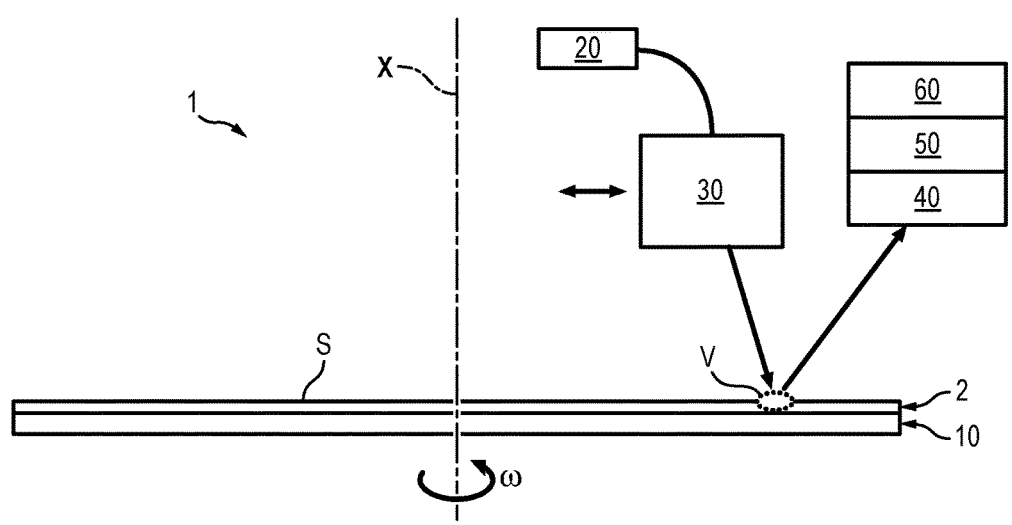
FIG. 2 is a schematic diagram of an inspection system according to the invention.

The principle of the inspection system 1 is shown in FIG. 2.

The system comprises a support 10 intended to receive a wafer 2 for inspection and to drive it in rotation about an axis of symmetry X perpendicular to a main surface S of said wafer. Generally, the wafer has a circular shape but the invention is applicable to any other shape.

The wafer 2 is held on the support 10 by any appropriate means, such as electrostatic means, mechanical means, etc.

The mechanism for rotating the support is known per se and therefore will not be described in detail.

The support 10 comprises one or more encoders (not shown) making it possible to know the angular position of the wafer at any moment.

The inspection system 1 also comprises a light source 20.

The light source 20 is typically a laser of distributed feedback laser (DFB) type.

The light source is coupled with an interferometric device 30 that will be described in detail below.

The inspection system comprises in addition a device 40 for collection of the light backscattered by the region of the wafer passing through the measurement volume. This device 40 can comprise an optical fibre, preferably with a large core diameter (i.e. typically between 100 and 1000 µm in diameter), the input of which is arranged facing the surface of the wafer, close to the measurement volume, and the output of which is coupled with a device 50 for capturing collected light in order to emit an electrical signal representing the variation in the light intensity of the collected light as a function of time. Said device 50 typically comprises a photodetector.

Preferably, the interferometric device 30 and the device 40 for the collection of the backscattered light are rigidly fixed together. In fact, the input of the collection device 40 must be positioned in an appropriate manner with respect to the measurement volume in order to receive the light backscattered by the wafer.

The interferometric device 30 comprises an optical waveguide the input of which is coupled with the light source 20 and which comprises two symmetrical branches for dividing the beam originating from the light source into two incident beams. At its end, each branch has an expanded portion intended to widen the beam while retaining its Gaussian profile. At the output of the optical waveguide, the branches are oriented in relation to one another so as to form, at the intersection between the two beams, a measurement volume V containing interference fringes.

Particularly advantageously, the interferometric device is in the form of an integrated optical device constituted by a single piece and ensuring both the separation of the beam emitted by the light source and the transmission of the two branches of the beam in order to form the interference volumes at the output of the sensor. It is noted that an integrated optical device is an optical device produced by microelectronic techniques.

The article "Integrated Laser Doppler Velocimeter for Fluid Velocity and Wall Friction Measurements" by P. Lemaitre-Auger et al. describes such an integrated optical device.

Such a device is produced in particular by the company A2 Photonic Sensors and marketed under the reference i-LDA™.

By way of example, the integrated optical device can be produced by ion exchange on a glass substrate. This process generally comprises:

providing a glass substrate,
depositing a metallic masking layer onto said glass substrate,
depositing a polymer layer onto the metallic layer,
transferring by photolithography a pattern defining the shape of the optical waveguide onto the polymer layer,
chemical etching of the metallic masking layer using a chemical process in the zones left exposed by the polymer mask,
removing the polymer mask,
immersing the substrate covered with the etched metallic masking layer in an ion bath (for example a potassium nitrate bath),
exchanging ions present in the bath (for example potassium ions) and ions contained in the glass (for example sodium ions) through zones of the substrate that are not covered by the metallic masking layer, the latter blocking the passage of the ions.

On account of the difference in size between the ions present in the bath and the ions present in the glass, the ion exchange generates local mechanical stresses in the glass substrate which increase the refractive index of the glass. The aforementioned guide is obtained in this way.

The metallic masking layer is then removed and optionally a protective layer, for example of $SiO_2$, is deposited. Finally, the edges of the substrate are cut out and they are finely polished.

There are other processes for the production of integrated optical devices and a person skilled in the art may choose from the microelectronic technologies at their disposal in order to design the integrated optical device.

Optionally, the optical device may also be combined with an optical fibre making it possible to collect the backscattered light.

An advantage of this integrated device is its robustness and its stability. In particular, unlike a system produced by other technologies such as micro-optics or optical fibres, the compact nature of the integrated device and the integration of the various components means that it is not sensitive to vibration and temperature gradients.

Furthermore, arrangements are made to ensure that the region in which each measurement volume extends has a thickness less than that of the wafer (this region including a portion of the surface to be inspected). The thickness of said region is preferably less than or equal to 90% of the thickness of the wafer. For example, for a wafer of 500 µm to 1 mm in thickness, arrangements are made so that the measurement volumes extend into a region of the wafer having a thickness less than or equal to 100 µm.

The dimension of the measurement volume is characteristic of the interferometric device and is defined by the angle between the two branches of the light guide in which the light beam emitted by the source propagates and by the numerical aperture of said branches. These characteristics are thus set during the production of the integrated optical device, which makes it possible to ensure good control of the performances of the system during its mass production.

Thus, it is possible to limit this measurement volume to the surface of the wafer or to a region of the neighbourhood of said surface.

In this way it is ensured that the defects detected are located on the surface to be inspected or its close neighbourhood, and not on the opposite surface of the wafer.

An integrated optical device has an additional advantage in this context, given that its stability makes it possible to avoid a depth-of-field error. The control of the depth of field permitted by the integrated device thus facilitates the inspection of transparent wafers by laser Doppler velocimetry.

It will be noted that by contrast, the control of the depth of field assumes a lesser importance for inspecting an opaque wafer, given that, since the measurement volume does not penetrate into the thickness of such a wafer, it is sufficient for a portion of the surface of the wafer to pass through the measurement volume in order to allow the inspection of said surface.

Finally, the inspection system 1 comprises a processing device 60 configured in order to detect, in said signal, a frequency component corresponding to the Doppler frequency.

The processing device 60 is advantageously coupled with an interface (not shown) making it possible for a user to access the results of the inspection so as in particular to display them, record them and/or print them.

According to a particularly advantageous embodiment of the invention, the inspection system is designed to produce a measurement volume containing interference fringes that are not parallel (i.e. not having a constant inter-fringe distance), but with an inter-fringe distance that varies within said measurement volume.

As will be explained below with reference to FIGS. 3A and 3B, the inter-fringe distance variation is chosen sufficiently large in order to allow a Doppler frequency to be obtained that is sufficiently different from one point to another of the measurement volume. This variation of the inter-fringe distance is obtained by the emission, by the source 20, of a light beam that is quasi-collimated, i.e. that has a divergence that is non-zero and less than 20°. By means of this property of the beams, the inter-fringe distance increases linearly in the direction of propagation of the beams.

As stated in the aforementioned article by Lemaitre-Auger, the inter-fringe distance depends on the wavelength of the light source, the optical index of the optical waveguide and the angle between the two branches of the light guide. For a given wavelength of the light source, the mean inter-fringe distance is thus fixed during the production of the integrated optical device, the variability of the inter-fringe distance being obtained by the quasi-collimated character of the beam emitted by the source.

In order to inspect a wafer, said wafer 2 is put in place on the support 10 and the support is driven in rotation at a controlled angular velocity ω. By means of the encoders present on the support 10, the angular position of a given point of the wafer is known at each moment. The velocity of rotation of the wafer is typically of the order of 5000 rpm.

In the inspection system 1, the interferometric device 30 is arranged facing a main surface of the wafer 2, on an arm (not shown) suitable for moving said device 30 in a radial direction. Thus, taking account of the rotation of the wafer, it is possible to successively sweep the entire surface of the wafer with the measurement volume by moving the interferometric device radially in translation as well as the device for collection of the backscattered light.

It is arranged for the interference fringes to extend transversally to the path of rotation of the wafer, perpendicular or inclined at a non-zero angle with respect to this path.

According to an embodiment (not shown), the measurement volume extends in a direction parallel to the normal to the main surface of the wafer. Such may be the case in particular when the inter-fringe distance is constant within the measurement volume.

According to a further embodiment, as shown in FIGS. 2A and 5A, the measurement volume is inclined at an angle θ with respect to the normal to the main surface S of the wafer 2.

The fringes are oriented substantially radially, preferably such that the inter-fringe distance varies between a minimum distance dmin at the furthest end of the measurement volume from the axis of rotation of the wafer and a maximum distance dmax at the closest end of the measurement volume to the axis of rotation of the wafer. The amplitude of variation from one end to the other of the measurement volume can be of the order of ±35% around a nominal value, and can range for example up to ±50% around a nominal value.

FIGS. 3A and 3B show the measurement volume with respect to the surface S of the wafer, respectively in side view and in top view. The distances d1 and d2 correspond to the inter-fringe distances at the intersections of the measurement volume with the wafer.

Figure 4B:
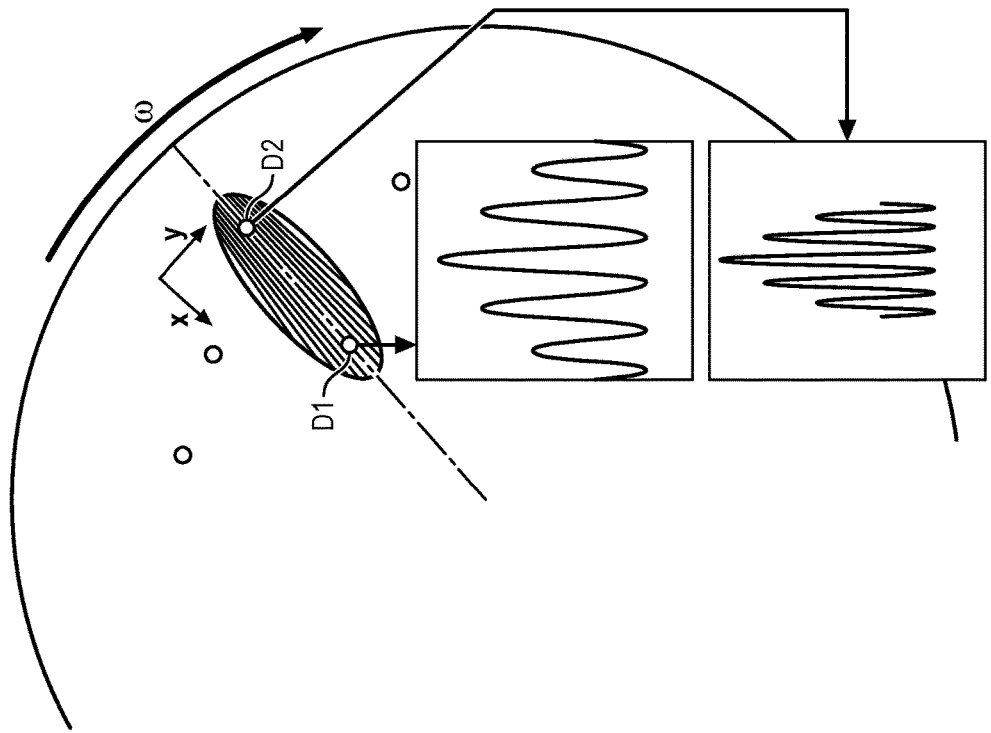
FIGS. 4A and 4B show diagrammatically the Doppler bursts obtained respectively for a measurement volume in which the interference fringes are parallel and for a measurement volume according to the first embodiment of the invention, in which the interference fringes have a variable spacing in the radial direction of the wafer.
Figure 4A:
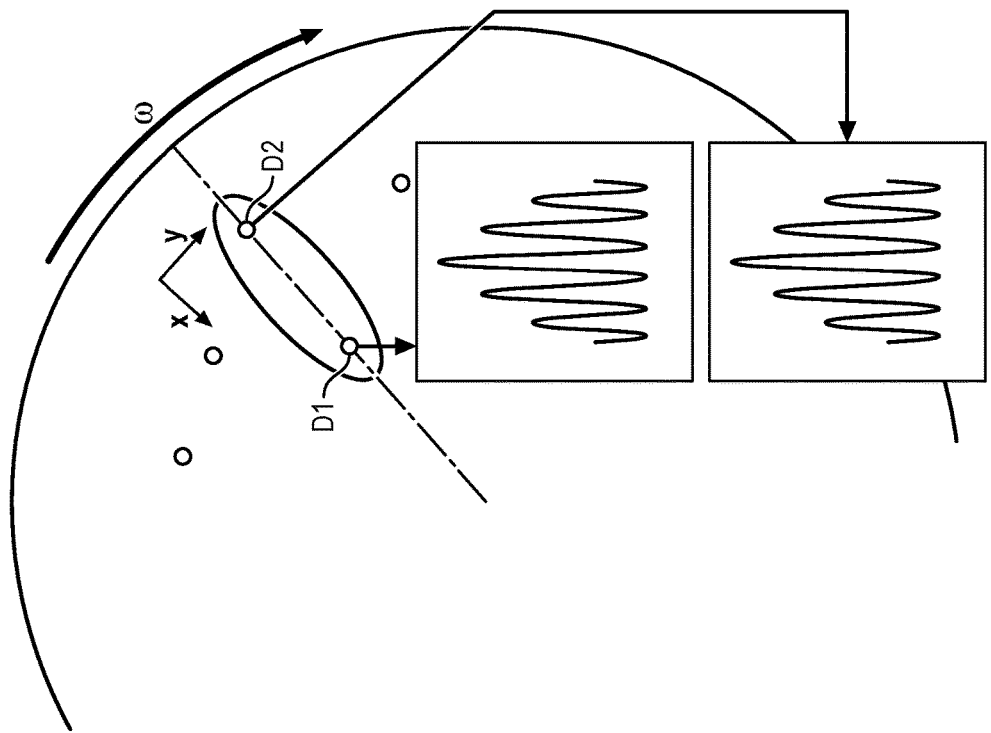

The effect of such a measurement volume on the resolution of detection of the radial position of a defect appears by comparison of FIGS. 4A and 4B.

FIG. 4A corresponds to an inspection method in which the inter-fringe distance is constant within the measurement volume V, i.e. the fringes are parallel. In this case, two defects D1 and D2 passing within said measurement volume V generate Doppler bursts of the same frequency. These Doppler bursts are shown in the two rectangles.

FIG. 4B corresponds to an inspection method according to an embodiment of the invention, in which the inter-fringe distance varies linearly, increasing towards the centre of the wafer. In this case, the defects D1 and D2 that pass through the measurement volume V pass through fringes having different inter-fringe distances and each generate a Doppler burst of a different frequency, since the frequency of the Doppler burst depends on the inter-fringe distance.

Thus, with the knowledge of the Doppler frequency and the velocity of the defect, it is possible to determine the position of said defect, with a higher resolution.

By way of example, the measurement volume can have the following dimensions: x*y*z=220*y*80 μm (the dimension not being significant in the case in question), and can be inclined by an angle θ=30° with respect to the normal to the surface S of the wafer. Generally, in this embodiment an angle comprised between 10 and 80° with respect to normal to the main surface of the wafer will be chosen. The inter-fringe distance can be chosen in order to measure 1.4 μm±10%, varying linearly in the radial direction x. Consequently, the minimum inter-fringe distance dmin is equal to 1.26 μm and the maximum inter-fringe distance is equal to 1.54 μm. In this configuration, the inter-fringe distance varies, in the portion of the measurement volume at the intersection with the wafer, between a value d1=1.37 μm and a value d2=1.43 μm, i.e. a variation of 0.06 μm from one end to the other of this portion of the measurement volume.

Figure 5:
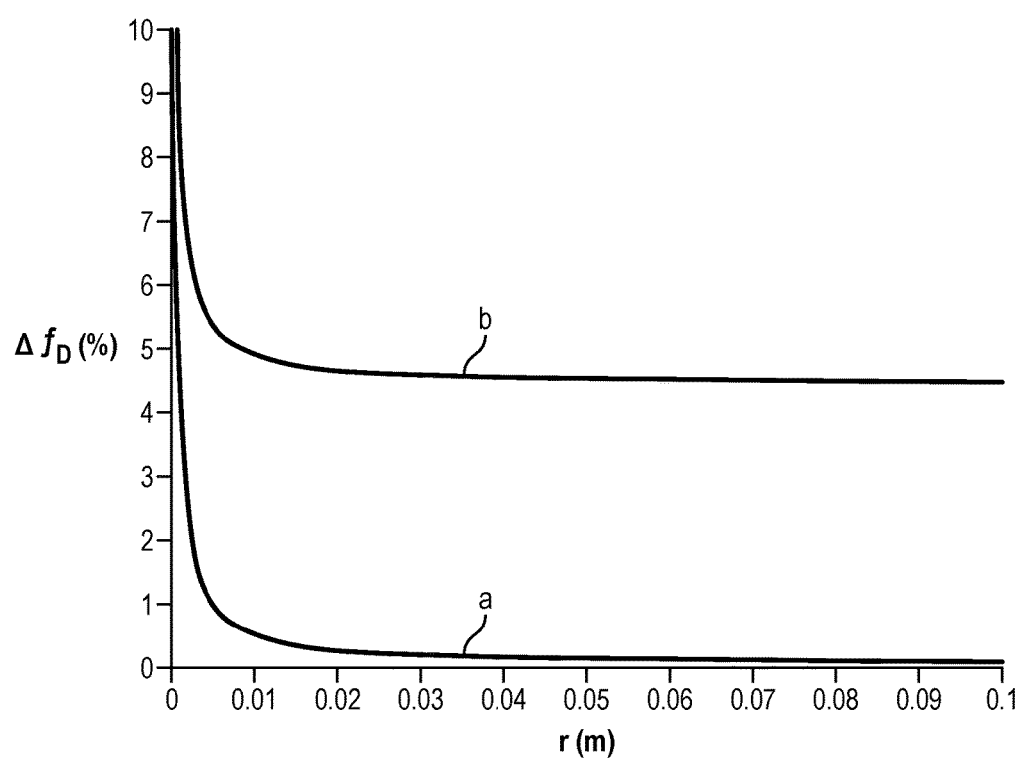
FIG. 5 shows the curves of variation in the Doppler frequency (in %) as a function of the distance r with respect to the centre of the wafer, for a measurement volume in which the interference fringes are parallel (curve (a)), and for a measurement volume according to the first embodiment of the invention (curve (b))

FIG. 5 shows the curves of variation in the Doppler frequency (in %) as a function of the distance r with respect to the centre of the wafer, for a measurement volume in which the interference fringes are parallel (curve (a)), and for a measurement volume according to the first embodiment of the invention (curve (b)).

It is observed that in the case of a constant inter-fringe distance, the variation in Doppler frequency is very small, with the exception of the central portion of the wafer.

On the other hand, in the case of an inter-fringe distance varying radially, the variation in the Doppler frequency from one end to the other of the measurement volume is a minimum of 4.5% and can thus be measured at any point of the surface of the wafer. Assuming that it is possible to detect frequency differences of the order of one percent, the use of a measurement volume having a variable inter-fringe distance makes it possible to increase by almost a factor of 5 the resolution of the determination of the radial position of the defects.

Apart from the improvement in the resolution of the determination of the radial position of the defects, the implementation of a measurement volume having a variable inter-fringe distance has the advantage of considerably simplifying the design of the interferometric device. In fact, in the known inspection systems, it is sought to obtain a perfect parallelism of the fringes so as to avoid measurement inaccuracies. This requirement involves severe constraints in the design and the production of the interferometric device. Working counter to the usual practice in the inspection field, the invention also makes it possible to dispense with design and production constraints and can thus be implemented much more easily than in the known inspection systems for opaque wafers.

Figure 6A:
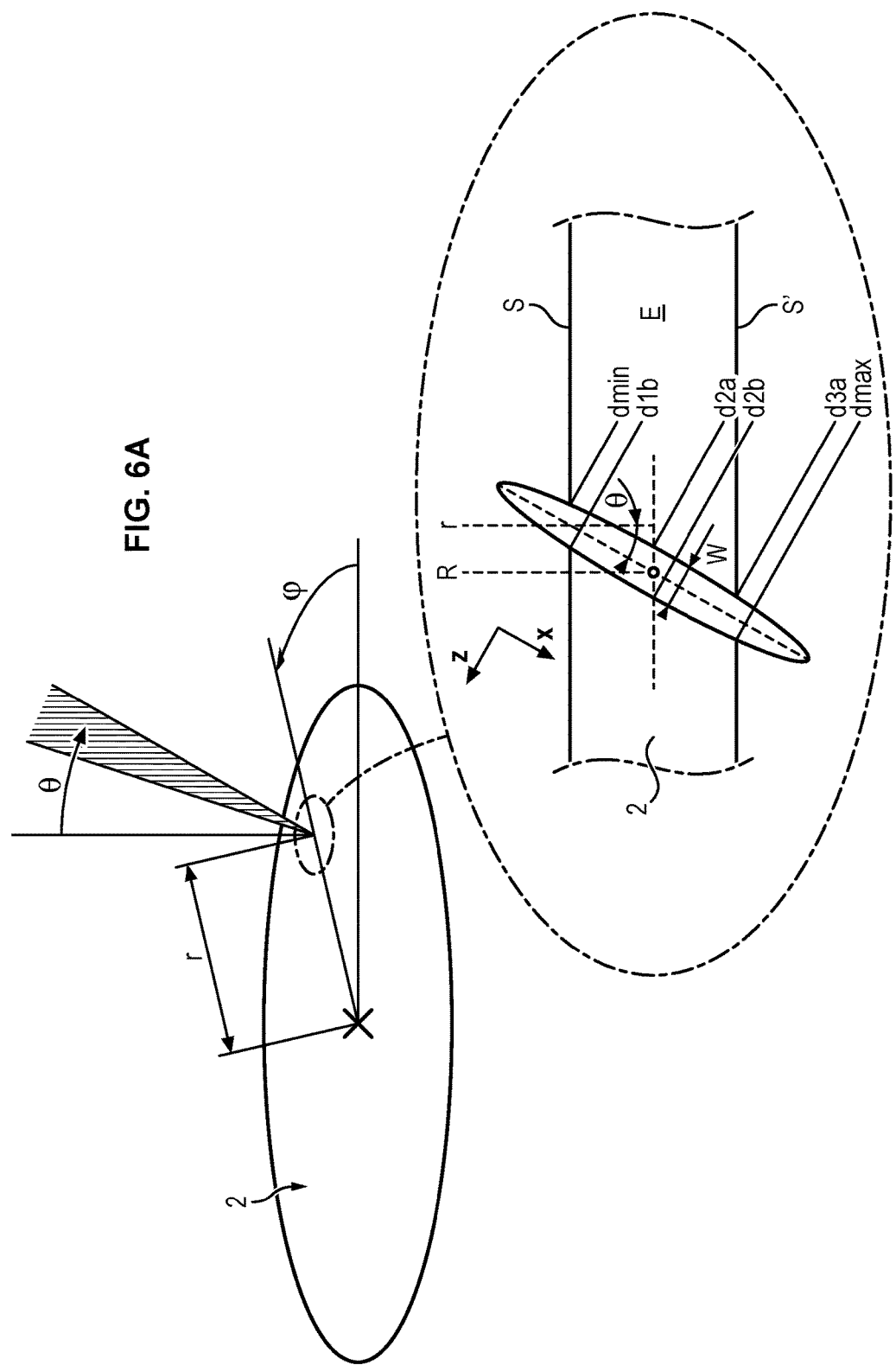

FIGS. 6A and 6B show a second embodiment of the invention. As in the first, a measurement volume is formed containing fringes in which the inter-fringe distance is variable. However, in this case, the measurement volume is inclined in a direction close to the normal to the surface of the wafer (angle θ of the order of 0 to 30°).

As the wafer is at least partially transparent at the wavelength of the incident beam, the measurement volume extends through the wafer 2. Consequently, regardless of the site of a defect (on the main surface S situated on the side of the interferometric device, on the opposite main surface S' or in the thickness E of the wafer), this defect generates a Doppler burst and can therefore be detected.

The variability of the inter-fringe distance makes it possible to determine more accurately the position of the defect in the direction of the thickness of the wafer. In fact, as can be seen in FIG. 6B, the inter-fringe distance varies linearly in the direction of the thickness and in the radial direction, between a minimum distance (dmin, d1b) and a maximum distance (d3a, dmax), passing via an intermediate distance (d2a, d2b) at the centre of the measurement volume. Thus, a defect present on the surface S does not generate a Doppler burst of the same frequency as a defect present in the thickness E or that of a defect present on the surface S'.

FIG. 7 is a logic diagram showing the different steps for locating a defect in the volume of the wafer.

The parameters mentioned in this figure are defined as follows:

r: radial position of the point of the surface swept by the measurement volume,

φ: tangential position of the point of the surface swept by the measurement volume, F: Doppler frequency detected (Doppler signature of the detected defect), Fd: theoretical Doppler frequency of a defect present on the surface of the wafer, at a radial distance r, x: ratio between the measured Doppler frequency and the theoretical Doppler frequency (x=F/Fd), T: thickness of the wafer,
D: deduced depth,
θ: angle between the measurement volume and the normal to the wafer,
R: actual radial position of the detected defect in the thickness of the wafer.

Given that the inter-fringe distance reduces linearly along the thickness of the wafer, the depth of the defect is given by the following formula:

$$D = \frac{(1-x)}{(1-0.8)} * T$$

Furthermore, given that the incident beams forming the measurement volume are inclined by an angle θ with respect to the normal to the surface of the wafer, a defect detected in the thickness of the wafer would not have r for its radial position but:

$R=r+D*\tan(\theta)$

In this approach, it is assumed that all the points of the measurement volume have the same linear velocity, i.e. no account is taken of the variation in the tangential velocity linked to the fact that the defects present at different depths in the wafer have a different radial position. However, as explained for the first embodiment, this phenomenon can optionally be exploited in the second embodiment in order to further improve the detection resolution.

As shown in FIG. 7, the method for the detection of a defect comprises the following steps.

Step 100 comprises capturing the backscattered light and emitting an electrical signal representing the intensity of the scattered light as a function of time, indicating the presence of a defect in or on the wafer.

Step 101 comprises determining the corresponding Doppler frequency, (marked F).

Step 102 comprises obtaining encoding data of the radial position of the detected defect and step 103 comprises determining, based on these data, the radial position r of said detected defect.

Step 104 comprises obtaining encoded data on the rotation of the wafer.

This makes it possible to determine on the one hand the velocity of rotation of the wafer (step 105) and the tangential position of the detected defect (angle φ) (step 106).

In step 107, the combination of the radial position of the defect and the velocity of rotation of the wafer makes it possible to determine the theoretical Doppler frequency of the defect (marked Fd).

Steps 108, 109 and 110 are calculation steps, respectively, of the ratio x between the detected Doppler frequency and the theoretical Doppler frequency of the defect, the depth D of the defect based on the formula disclosed above, then the actual radial position R of the defect, according to the formula disclosed above.

Finally, in step 111, the combination of the results of these calculations and of the angle φ makes it possible to determine the position (X, Y, Z) of the defect in the three directions.

The detection method that has just been described makes it possible, by means of a measurement volume that extends through the thickness of the wafer, to detect a defect regardless of its site in the direction of the thickness of the wafer.

It can however be beneficial, in certain situations, to seek to limit the dimension of the measurement volume in the direction of the thickness of the wafer.

To this end, the invention can comprise, in a particular embodiment, the use of a band-pass filter, having a high selectivity.

Figure 8:
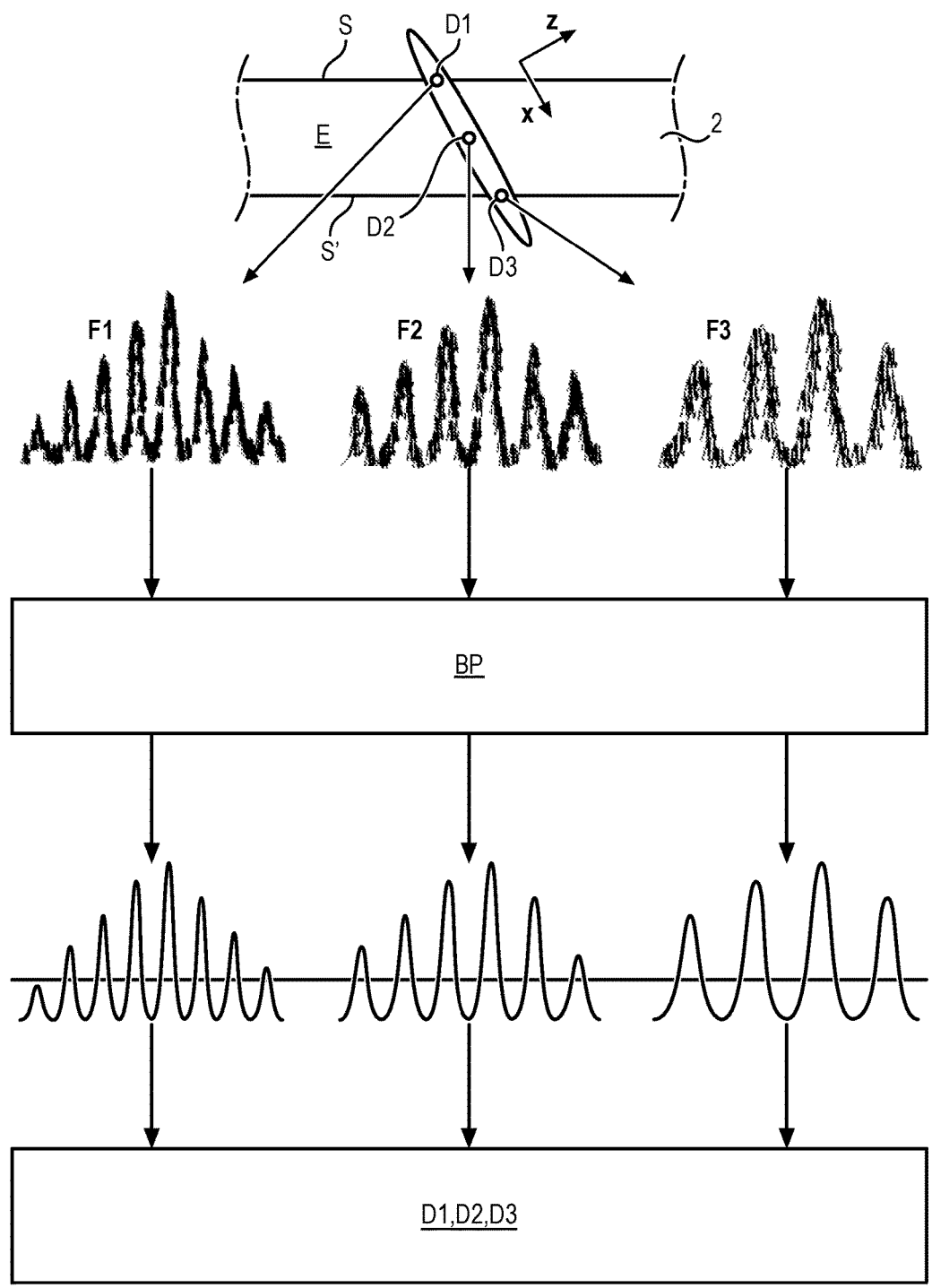
FIG. 8 shows the detection of defects in different sites in the thickness of the wafer according to the second embodiment, utilizing a conventional band-pass filter.
Figure 9:
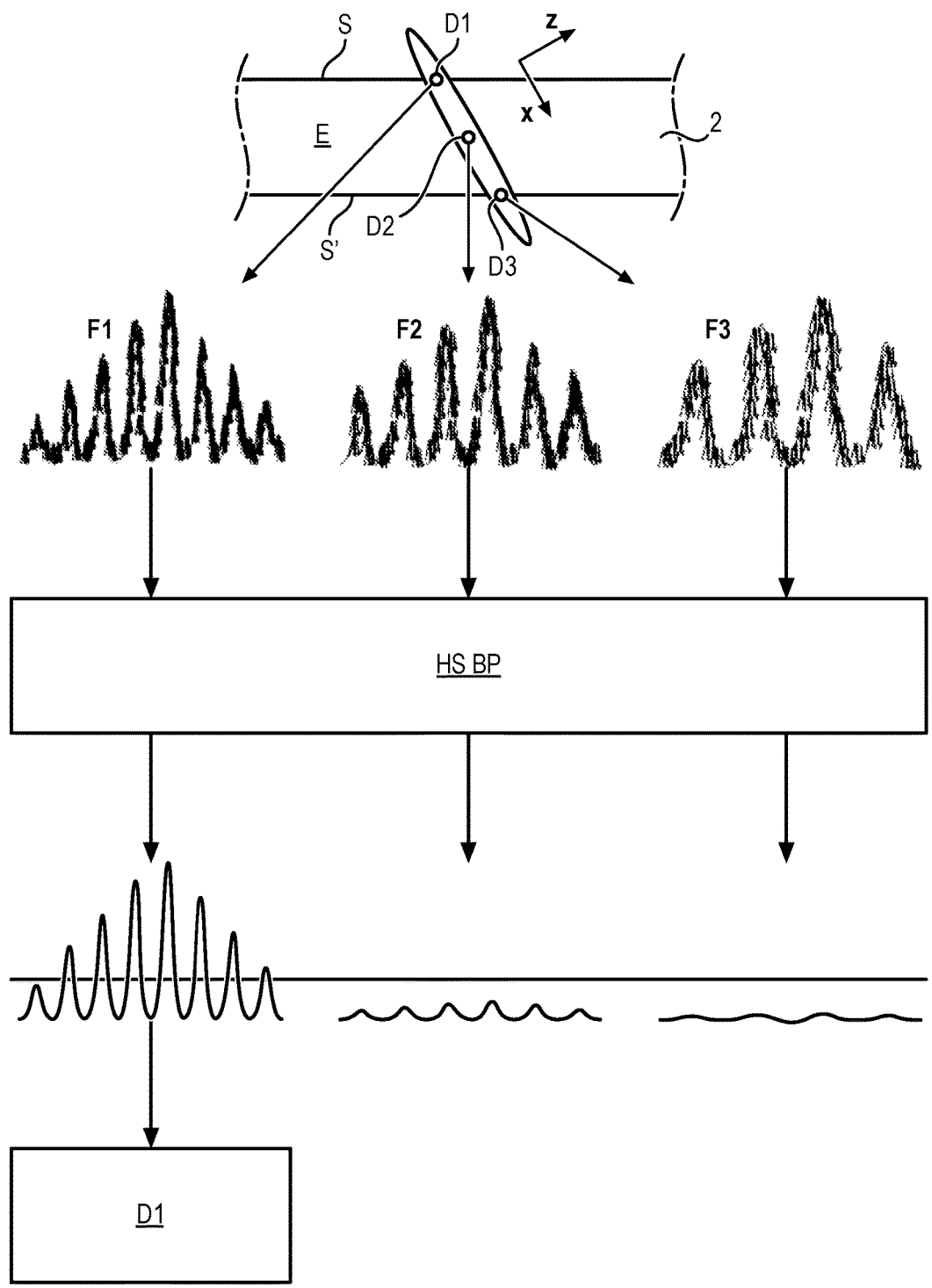
FIG. 9 shows the detection of defects in a site determined in the thickness of the wafer, according to the second embodiment in combination with a high-selectivity band-pass filter.

As shown in FIG. 8, a band-pass filter BP is generally used in order to allow to pass, in the electrical signal, only the Doppler frequency associated with the measurement volume and a narrow range of frequencies around this frequency. If it is desired to detect a defect regardless of its site in the thickness of the wafer, this filter has a moderate selectivity, in order to take account of the variation in Doppler frequency due to the variation in the inter-fringe distance from one face of the wafer to the other. Such a filter therefore supplies a filtered signal that contains the Doppler signature F1, F2, F3, of a respective defect D1, D2, D3, regardless of its site.

So as to detect selectively only the defects present at a determined depth in the thickness of the wafer, a highly selective filter is utilized, i.e. a filter the pass-band of which corresponds exactly to the Doppler frequency associated with this depth, and which does not allow any other frequency to pass. Given that the inter-fringe distance is variable in the direction of the thickness of the wafer, each depth is in fact associated with a different Doppler frequency. Thus, in the example shown, the filter HS BP selects the frequency F1 which is the Doppler frequency associated with the main surface S of the wafer. This means that the output signal of the filter will contain only the Doppler frequency of the defect D1 present on this surface, but not that of the defect D2 present in the thickness E of the wafer nor of the defect D3 present on the opposite surface S'.

By means of this filtering, the measurement volume is thus reduced in the direction of the thickness.

Furthermore, given that the measurement volume is inclined with respect to the normal to the main surface of the wafer, said filtering also has the effect of reducing the measurement volume in the radial direction. In fact, as shown in FIG. 6B which has been described above, the inter-fringe distance at the surface S of the wafer varies between a value d1$a$ and a value d1$b$. By selecting a filter the pass-band [$d_{start}$–$d_{end}$] of which is such that d1$a$<$d_{start}$<$d_{end}$<d1$b$, the measurement volume is reduced in the radial direction.

By way of example, the inventors have produced a system comprising an integrated optical device such as described above, making it possible to form a measurement volume of 300 μm in depth (in the direction of the thickness of the wafer) and having an inter-fringe distance varying between 0.8 and 1.2 μm. In the case where a defect passes through this volume at a velocity of 10 m/s, the associated Doppler frequencies are comprised between 12.5 Mhz and 8.3 Mhz.

If a measurement volume is sought that is centred on an inter-fringe distance of 1 μm and having a depth of 50 μm (which corresponds to a variation in the inter-fringe distance between 0.95 and 1.05 μm), a filter must be applied having a pass-band from 9.5 MHz to 10.5 MHz. The greater the slopes of this band-pass filter, the higher the selectivity of the filter.

If a measurement volume of 10 μm is sought, the pass-band ranges from 9.9 MHz and 11 MHz.

Naturally, the characteristics of the filter depend on the velocity of the defects, but a person skilled in art is able to determine, as a function of the speed of rotation of the wafer, the suitable pass-band of the filter in order to obtain a determined measurement volume.

REFERENCES

WO 2009/112704
WO 02/39099
Integrated Laser Doppler Velocimeter for Fluid Velocity and Wall Friction Measurements, P. Lemaitre-Auger, A. Cartellier, P. Benech and Schanen Duport, Sensors, 2002, Proceedings of IEEE (Vol:1), pp. 78-82.

The invention claimed is:

1. A method for inspecting a wafer for electronics, optics or optoelectronics, comprising:
    rotating the wafer about an axis of symmetry perpendicular to a main surface of said wafer;
    emitting, from a light source coupled with an interferometric device, two quasi-collimated incident light beams, so as to form, at the intersection between the two beams, a measurement volume containing interference fringes extending transversally to the path of rotation of the wafer and having a variable inter-fringe distance within the measurement volume, the time signature of the passage of a defect through the measurement volume depending on the value of the inter-fringe distance at the location where the defect passes through the measurement volume, said wafer being at least partially transparent at the wavelength of the light source;
    the interferometric device and the wafer being arranged in relation to one another so that the measurement volume extends into a region of the wafer, the thickness of said region being less than the thickness of the wafer;
    collecting at least a portion of the light scattered by said region of the wafer,
    capturing the collected light and emitting an electrical signal representing the variation in the light intensity of the collected light as a function of time;
    detecting, in said signal, a frequency component in the variation of the intensity of said collected light, said frequency being the time signature of the passage of a defect through the measurement volume; and
    determining, based on the value of the inter-fringe distance at the location where the defect passes, the position of said defect in the radial direction and/or in the thickness of the wafer.

2. The method according to claim 1, in which said interferometric device is an integrated optical device comprising a light guide the input of which is coupled with the light source and which is divided into two branches, the output of which is oriented in order to form said measurement volume at the intersection of the two beams.

3. The method according to claim 1, in which the inter-fringe distance varies in the radial direction of the wafer.

4. The method according to claim 1, in which the inter-fringe distance varies between a minimum distance at the furthest end of the measurement volume from the axis of rotation of the wafer and a maximum distance at the closest end of the measurement volume to the axis of rotation of the wafer.

5. The method according to claim 1, in which in the measurement volume, the inter-fringe distance varies within an interval of ±50% around a nominal value.

6. The method according to claim 1, in which the measurement volume is inclined by an angle comprised between 10 and 80° with respect to the normal to the main surface of the wafer.

7. The method according to claim 1, in which the measurement volume is inclined by an angle comprised between 0 and 40° with respect to the normal to the main surface of the wafer.

8. The method according to claim 7, also comprising the utilization of a band-pass filtering of the signal, the pass-band of said filter being selected so as to transmit only the portion of the signal having the Doppler frequency associated with a determined position in the thickness of the wafer.

9. A system for inspecting wafers for electronics, optics or optoelectronics, comprising:
- a device for driving a wafer in rotation about an axis of symmetry perpendicular to a main surface of said wafer;
- a light source suitable for emitting a quasi-collimated light beam the wavelength of which is chosen so that at least a portion of said beam is transmitted through the wafer;
- an interferometric device coupled with the light source in order to divide the beam emitted by said source into two beams and in order to form, at the intersection between the two beams, a respective measurement volume containing interference fringes, the inter-fringe distance being variable within said measurement volume;
- a device for collecting light scattered by the wafer;
- a device for capturing collected light configured in order to emit an electrical signal representing the variation in the light intensity of the collected light as a function of time; and
- a processing device configured in order to detect, in said signal, a frequency component in the variation of the intensity of said collected light, said frequency being the time signature of the passage of a defect through a respective measurement volume and dependent on the value of the inter-fringe distance at the location where the defect passes through the measurement volume and in order to determine, based on said frequency, said value for the inter-fringe distance and the position of the defect in the radial direction and/or in the thickness of the wafer.

10. The system according to claim 9, in which the interferometric device is an integrated optical device.

11. The system according to claim 9, also comprising an arm for moving the interferometric device and the device for the collection of scattered light in translational motion in a radial direction.

* * * * *